(12) United States Patent
Downs et al.

(10) Patent No.: US 6,683,198 B1
(45) Date of Patent: Jan. 27, 2004

(54) GROUP(III)-METAL-HYDRIDES WITH A GUANIDINO-TYPE LIGAND

(75) Inventors: Anthony John Downs, Oxford (GB); Hans-Jörg Himmel, Oxford (GB)

(73) Assignee: Isis Innovation Limited, Oxford (GB)

( * ) Notice: Subject to any disclaimer, the term of this patent is extended or adjusted under 35 U.S.C. 154(b) by 51 days.

(21) Appl. No.: 10/049,281

(22) PCT Filed: Aug. 9, 2000

(86) PCT No.: PCT/GB00/03070

§ 371 (c)(1),
(2), (4) Date: Feb. 21, 2002

(87) PCT Pub. No.: WO01/12634

PCT Pub. Date: Feb. 22, 2001

(30) Foreign Application Priority Data

Aug. 12, 1999 (GB) .............................................. 9919071

(51) Int. Cl.$^7$ ........................... C07F 5/00; C23C 16/00; H01L 21/44
(52) U.S. Cl. .............................. 556/1; 556/21; 556/23; 556/36; 556/178; 556/18; 427/584; 427/587; 427/593; 438/608; 438/681; 438/796
(58) Field of Search ................................. 556/1, 36, 18, 556/21, 23; 427/584, 587, 593; 438/608, 681, 796

(56) References Cited

U.S. PATENT DOCUMENTS

| | | | |
|---|---|---|---|
| 4,740,606 A | 4/1988 | Melas | 556/1 |
| 4,792,467 A | 12/1988 | Melas et al. | 427/248.1 |
| 5,112,432 A | 5/1992 | Erdmann et al. | 156/610 |
| 5,120,676 A | 6/1992 | Melas et al. | 437/81 |

FOREIGN PATENT DOCUMENTS

EP 0399190 11/1990

OTHER PUBLICATIONS

Chemical Abstracts, Abstract No. 126:321309 Leon et al J. Phys. Chem. A (1997), 101 (13), 2489–2495.
Chemical Abstracts, Abstract No. 72:85717 Snaith et al. J. Chem. Soc. A (1970), (3), 380–3.
Snaith et al., journal of the Chemical Society [Section A]: Inorganic, Physical, Theoretical (1970), vol. 3, pp. 380–383.*

* cited by examiner

*Primary Examiner*—Porfirio Nazario-Gonzalez
(74) *Attorney, Agent, or Firm*—Nixon & Vanderhye P.C.

(57) ABSTRACT

A compound of formula (I)

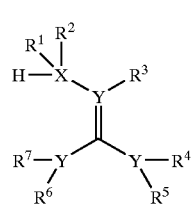

wherein
X is aluminium, gallium or indium;
each Y, which may be the same or different, is nitrogen or phosphorus;
$R^1$ and $R^2$, which may be the same or different, are hydrogen, halogen or alkyl; and
$R^3$ to $R^7$, which may be the same or different, are hydrogen or a saturated group,
or $R^3$ and $R^4$, or $R^5$ and $R^6$ together represent a saturated divalent link thus completing a ring.

10 Claims, No Drawings

GROUP(III)-METAL-HYDRIDES WITH A GUANIDINO-TYPE LIGAND

This application is the US national phase of international application PCT/GB00/03070 filed Aug. 9, 2000, which designated the US.

The present invention relates to Group III metal compounds, processes for their preparation and their use in deposition. The invention in particular relates to gallium compounds, processes for their preparation and their use, for example in the vapour deposition of a gallium layer or a III–V semiconductor layer.

The epitaxy of III–V semiconductors is used in the fabrication of very thin semiconductor layers. These layers are highly efficient because of the "quantum well" effect. The layers are usually formed either by epitaxy from solution or by gas phase or molecular beam epitaxy.

Although epitaxy from solution is the most economical method, the size of the structure which can be obtained is severely limited and very thin structures cannot be fabricated. Molecular beam epitaxy is the most expensive method and is consequently used mainly for scientific research. As a result of the limitations of solution and molecular beam epitaxy, gas phase epitaxy is commonly adopted. Generally gas phase epitaxy is not very expensive and allows the fabrication of very thin structures. For example, the reaction of $Ga(CH_3)_3$ with $AsH_3$ is used for the deposition of GaAs layers:

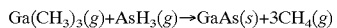

$$Ga(CH_3)_3(g) + AsH_3(g) \rightarrow GaAs(s) + 3CH_4(g)$$

However, $Ga(CH_3)_3$ is not an ideal source of gallium because the presence of a relatively strong Ga—C bond is liable to give rise to carbon impurities in the semiconductor layer which is formed. The efficiency of a semiconductor is significantly reduced by the presence of even small amounts of impurities. Therefore, there is a need to develop stable gallium compounds which are volatile and which decompose completely on pyrolysis at a surface to give gallium and volatile organic or other molecules.

The present invention provides stable Group III metal compounds which are volatile and which on decomposition give the Group III metal and other products which are stable and volatile. The compounds may be used, for example, in the vapour deposition of a Group III metal layer or a III–V semiconductor layer.

Accordingly the present invention provides a compound of formula (I)

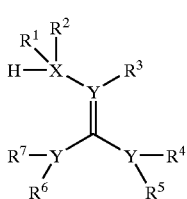

(I)

wherein
X is aluminium, gallium or indium,
each Y, which may be the same or different, is nitrogen or phosphorus;
$R^1$ and $R^2$, which may be the same or different, are hydrogen, halogen or alkyl; and $R^3$ to $R^7$, which may be the same or different, are hydrogen or a saturated group,
or $R^3$ and $R^4$, or $R^5$ and $R^6$ together represent a saturated divalent link thus completing a ring.

The term "halogen" as used herein means fluorine, chlorine, bromine and iodine.

The term "alkyl" as used herein includes both straight and branch chain radicals. Typically it is $C_1$ to $C_6$ alkyl, preferably $C_1$ to $C_4$ alkyl, for example methyl, ethyl, i-propyl, n-propyl, t-butyl, s-butyl, or n-butyl. It may also be pentyl, hexyl and the various branch chain isomers thereof The term "saturated group" as used herein means a group in which the atoms are linked by single bonds. Typically it includes alkyl, silyl and trialkylsilyl.

The term "saturated divalent link" as used herein means a chain in which the atoms are linked by single bonds, for example alkylene.

The term "ring" as used herein typically includes five to eight membered rings, especially five and six membered rings.

X is preferably gallium.

Each Y is preferably nitrogen.

$R^1$ and $R^2$ are preferably hydrogen, chlorine or methyl.

$R^3$ to $R^7$ are preferably hydrogen, alkyl, silyl or trialkylsilyl. More preferably $R^3$ to $R^7$ are hydrogen, methyl, silyl or trimethylsilyl. Most preferably $R^3$ to $R^7$ are hydrogen or methyl.

A preferred compound of formula (I) according to the present invention is 1,1,3,3-tetramethylguanidine-gallane.

The compounds of formula (I) may be prepared by the reaction of a Group III metal hydride source with a base of formula (II)

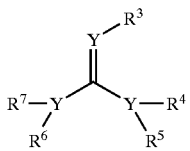

(II)

wherein Y and $R^3$ to $R^7$ are as defined above, or a salt thereof.

The Group III metal hydride source is typically $LiXR^1R^2H_2$, $R^1R^2HX$ or $R^1R^2HXRNMe_3$ wherein X, $R^1$ and $R^2$ are as defined above. Group III metal hydride sources may be prepared by reaction of a suitable Group III metal compound with $LiXH_4$ wherein X is as defined above. For example, gallium hydride adducts of a particular base may be prepared as follows:

$$LiGaH_4 + base \cdot HCl \longrightarrow base \cdot GaH_3 + LiCl + H_2$$

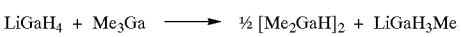

$$LiGaH_4 + Me_3Ga \longrightarrow \tfrac{1}{2}[Me_2GaH]_2 + LiGaH_3Me$$

$$\downarrow base$$

$$base \cdot GaMe_2H$$

Salts of the bases of formula (II) suitable for use according to the present invention include both inorganic salts, for example the hydrochloric salt, the hydrobromic salt and the hydroiodic salt, and organic salts, for example the trifluoroethanoate salt. Preferably the salts of the bases of formula (II) are hydrochloride salts.

When a salt of a base of formula (II) is used, the process is generally carried out in the presence of a solvent. The process may be carried out in the absence of a solvent when a free base of formula (II) is used.

The process needs to be carried out with rigorous exclusion of air and moisture; it may be carried out in the gas phase or the liquid phase. Typically the process is carried out at low temperature, for example −78° C., and under vacuum.

In one embodiment the compounds of formula (I) may be prepared commercially by producing a chemically unstable Group III metal hydride source, for example gallium hydride, in the locality of the preparation plant by methods known in the art. The hydride may then be treated with an amine, for example trimethylamine, to form a relatively storage-stable hydride-amine complex. A base of formula (II) can then be introduced into or mixed with the amine-hydride complex in the gas phase to displace the amine. Amines such as trimethylamine are very volatile leaving groups and allow the compounds of formula (I) to be condensed in high purity; the unused amine can be recovered and used for a subsequent batch.

The compounds of formula (I) can be used in deposition according to methods known in the art; The compounds may be used in vapour deposition to form a Group III metal layer or a III–V semiconductor layer. The compounds of formula (I) may be decomposed by, for example, thermolysis or photolysis. A III–V semiconductor layer may be prepared by decomposition of a compound of formula (I) with, for example, ammonia to form the Group III metal nitride layer, or with arsine, phosphine, stibine or other volatile compound of arsenic, phosphorus or antimony to form the Group III metal arsenide, phosphide or antimonide layer, respectively.

The Example which follows further illustrates the present invention.

EXAMPLE

Synthesis and Properties of 1,1,3,3-Tetramethylguanidine-Gallane ($H_3Ga.TMG$)

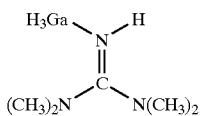

0.7 g of freshly synthesized $LiGaH_4$ is dissolved under nitrogen in dry $Et_2O$ and cooled to −78° C. 2.0 g 1,1,3,3,-tetramethylguanidine HCl (synthesised by condensing HCl on 1,1,3,3-tetramethylguanidine at −170° C. under nitrogen) are added while stirring during 30 min. The mixture is then warmed to room temperature and stirred for another 2 h. After the solution has been filtered, the solvent is removed in vacuo. 0.5 g of a light yellow raw product is isolated. This is purified by sublimation in vacuo (temp. 50–55° C., $10^{-5}$ torr) onto a cold finger (at 0° C.). 0.4 g of light yellow crystals is obtained.

$^1$H-NMR ($d_8$-toluene solution, 20° C.): 4.82 (3H, $GaH_3$), 4.14 (1H, NH), 2.45 (6H, cis-$N(CH_3)_2$), 1.90 (6H, trans-N$(CH_3)_2$).

Physical Properties:

Light yellow, crystalline solid at room temperature, mp 55° C.

Chemical Properties:

Stable at temperatures up to 85–90° C. but decomposes at higher temperatures to gallium, hydrogen and 1,1,3,3-tetramethylguanidine as shown in the Scheme below (stable for several weeks under nitrogen at room temperature and stable for at least 2 h under air).

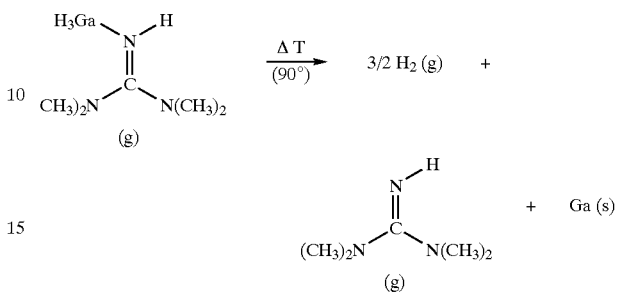

Scheme: Thermally induced decomposition of 1,1,3,3-tetramethylguanidine-gallane to Ga metal and volatile products (1,1,3,3-tetramethylguanidine and hydrogen).

Matrix-investigations:

Matrix isolation investigations allow the characterization of volatile compounds and the study of reaction pathways, e.g. photoinduced decomposition. Matrix studies may be used to demonstrate that the compounds according to the present invention can be evaporated without decomposition. Additionally, the stability of the compounds can be tested and decomposition pathways explored.

A compound is condensed in high vacuum ($<10^{-6}$ torr) together with an inert, IR-transparent gas (e.g. Ar) on a CsI window, which is kept at 10K. The inert gas is the host (matrix) and the compound is embedded in the solid Ar deposit. The compound is kept at extremely low temperatures and is therefore isolated in the inert matrix, allowing even highly unstable intermediates to be identified and studied.

Evaporation of 1,1,3,3-tetramethylguanidine-gallane, $H_3Ga.TMG$, at room temperature has been studied by matrix isolation of the vapour species. For comparison, trimethylamine-gallane and quinuclidine-gallane have also been matrix-isolated in separate experiments and the IR spectra of all three compounds recorded. The strong absorptions due to Ga—H stretching modes prominent in all the experiments (see Table) reveal that all three compounds have a significant vapour pressure at ambient temperatures and can be evaporated without decomposition.

| IR mode | $H_3Ga.NMe_3$ | $H_3Ga.quinuclidine$ | $H_3Ga.TMG$ |
|---|---|---|---|
| $v_s(H_3Ga)$ [cm$^{-1}$] | 1853.4 | 1837.0 | 1819.0 |
| $v_{as}(H_3Ga)$ [cm$^{-1}$] | 1832.3 | 1831.8 | 1812.1 |

Table: Frequencies (cm$^{-1}$) of the antisymmetric and symmetric Ga—H stretching modes in three different matrix-isolated gallane adducts.

Photolysis experiments reveal that 1,1,3,3-tetramethylguanidine-gallane is highly photolabile. On broadband photolysis (200–900 nm, 800 W), the Ga—H signals disappear, indicating decomposition of the molecule. It is believed that elimination of $H_2$ may be the first step in the decomposition.

What is claimed is:

1. A compound of formula (I)

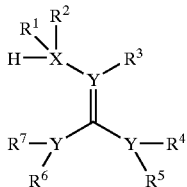
(I)

wherein
X is aluminium, gallium or indium;
each Y, which may be the same or different, is nitrogen or phosphorus;
$R^1$ and $R^2$, which may be the same or different, are hydrogen, halogen or alkyl; and
$R^3$ to $R^7$, which may be the same or different, are hydrogen or a saturated group,
or $R^3$ and $R^4$, or $R^5$ and $R^6$ together represent a saturated divalent link thus completing a ring.

2. A compound according to claim 1, wherein X is gallium.

3. A compound according to claim 1, wherein each Y is nitrogen.

4. A compound according to claim 1, wherein $R^1$ and $R^2$, which may be the same or different, are hydrogen, chlorine or methyl.

5. A compound according to claim 1, wherein $R^3$ to $R^7$ are hydrogen, alkyl, silyl or trialkylsilyl.

6. A compound according to claim 1, wherein $R^3$ to $R^7$ are hydrogen or methyl.

7. A compound according to claim 1, which is 1,1,3,3-tetramethylguanidine-gallane.

8. A process for preparing a compound of formula (I) as claimed in claim 1, which process comprises the reaction of a Group II metal hydride source with a base of formula (II)

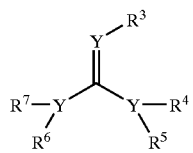
(II)

wherein Y and $R^3$ and $R^7$ are as defined in claim 1, or a salt thereof.

9. A method for forming a Group III metal layer which comprises forming a layer of a compound of formula (I) as claimed in claim 1 by vapor deposition, and decomposing the compound of formula (I) by thermolysis or photolysis.

10. A method for forming a III–V semiconductor layer which comprises forming a layer of a compound of formula (I) as claimed in claim 1 by vapor deposition, and decomposing the compound of formula (I) with ammonia, arsine, phosphine, stibine or other volatile compound of arsenic, phosphorus or antimony.

* * * * *